(12) United States Patent
Andreas et al.

(10) Patent No.: US 7,270,668 B2
(45) Date of Patent: Sep. 18, 2007

(54) APPARATUS AND METHODS FOR DELIVERING COILED PROSTHESES

(75) Inventors: Bernard Andreas, Redwood City, CA (US); Ron French, Santa Clara, CA (US); Allan Will, Atherton, CA (US)

(73) Assignee: Xtent, Inc., Menlo Park, CA (US)

( * ) Notice: Subject to any disclaimer, the term of this patent is extended or adjusted under 35 U.S.C. 154(b) by 0 days.

(21) Appl. No.: 10/306,622

(22) Filed: Nov. 27, 2002

(65) Prior Publication Data

US 2003/0130683 A1    Jul. 10, 2003

Related U.S. Application Data

(60) Provisional application No. 60/336,767, filed on Dec. 3, 2001.

(51) Int. Cl.
*A61F 11/00* (2006.01)

(52) U.S. Cl. ............ 606/108; 623/1.16; 623/1.22

(58) Field of Classification Search ......... 623/1.12, 623/1.23, 1.11, 1.1, 1.16
See application file for complete search history.

(56) References Cited

U.S. PATENT DOCUMENTS

| | | | |
|---|---|---|---|
| 4,468,224 A | | 8/1984 | Enzmann et al. |
| 4,512,338 A | * | 4/1985 | Balko et al. ............ 606/108 |
| 4,564,014 A | | 1/1986 | Fogarty et al. |
| 4,580,568 A | | 4/1986 | Gianturco |
| 4,681,110 A | | 7/1987 | Wiktor |
| 4,733,665 A | | 3/1988 | Palmaz |
| 4,739,762 A | | 4/1988 | Palmaz |
| 4,762,129 A | | 8/1988 | Bonzel |
| 4,775,337 A | | 10/1988 | Van Wagener et al. |
| 4,776,337 A | | 10/1988 | Palmaz |
| 4,886,062 A | | 12/1989 | Wiktor |
| 4,988,356 A | | 1/1991 | Crittenden et al. |
| 4,994,066 A | | 2/1991 | Voss |
| 4,994,069 A | * | 2/1991 | Ritchart et al. ............ 606/191 |

(Continued)

FOREIGN PATENT DOCUMENTS

EP    203945 B2 B2    12/1986

(Continued)

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

(Continued)

*Primary Examiner*—Corrine McDermott
*Assistant Examiner*—Christopher Daniel Prone
(74) *Attorney, Agent, or Firm*—Townsend and Townsend and Crew LLP; Jeffry J. Grainger, Esq.

(57) ABSTRACT

Methods and apparatus for delivering prostheses to body lumens, such as stents and grafts to blood vessels, utilize a delivery device which carries one or more linearized elements. The linearized elements assume non-linear configurations, particularly helical configurations, when advanced and released from the delivery device. By selectively controlling the length and/or number of elements delivered from the delivery device, extended and disseminated disease within the body lumens may be effectively treated.

17 Claims, 4 Drawing Sheets

U.S. PATENT DOCUMENTS

| | | | |
|---|---|---|---|
| 5,040,548 A | 8/1991 | Yock | |
| 5,092,877 A | 3/1992 | Pinchuk | |
| 5,102,417 A | 4/1992 | Palmaz | |
| 5,104,404 A | 4/1992 | Wolff | |
| 5,135,535 A | 8/1992 | Kramer | |
| 5,195,984 A | 3/1993 | Schatz | |
| 5,217,495 A | 6/1993 | Kaplan et al. | |
| 5,226,913 A | 7/1993 | Pinchuk | |
| 5,246,421 A | 9/1993 | Saab | |
| 5,273,536 A | 12/1993 | Savas | |
| 5,282,824 A | 2/1994 | Gianturco | |
| 5,300,085 A | 4/1994 | Yock | |
| 5,312,415 A | 5/1994 | Palermo | |
| 5,334,187 A | 8/1994 | Fischell et al. | |
| 5,421,955 A | 6/1995 | Lau | |
| 5,458,615 A | 10/1995 | Klemm et al. | |
| 5,478,349 A | 12/1995 | Nicholas | |
| 5,490,837 A | 2/1996 | Blaeser et al. | |
| 5,496,346 A | 3/1996 | Horzewski et al. | |
| 5,501,227 A | 3/1996 | Yock | |
| 5,507,768 A | 4/1996 | Lau et al. | |
| 5,507,771 A | 4/1996 | Gianturco | |
| 5,514,093 A | 5/1996 | Ellis et al. | |
| 5,514,154 A | 5/1996 | Lau et al. | |
| 5,527,354 A | 6/1996 | Fontaine et al. | |
| 5,549,551 A | 8/1996 | Peacock, III et al. | |
| 5,549,563 A | 8/1996 | Kronner | |
| 5,549,635 A | 8/1996 | Solar | |
| 5,554,181 A | 9/1996 | Das | |
| 5,562,725 A | 10/1996 | Schmitt et al. | |
| 5,571,086 A | 11/1996 | Kaplan et al. | |
| 5,593,412 A | 1/1997 | Martinez et al. | |
| 5,607,444 A | 3/1997 | Lam | |
| 5,607,463 A | 3/1997 | Schwartz et al. | |
| 5,628,775 A | 5/1997 | Jackson et al. | |
| 5,634,928 A | 6/1997 | Fischell et al. | |
| 5,662,675 A | 9/1997 | Polanskyj Stockert et al. | |
| 5,676,654 A | 10/1997 | Ellis et al. | |
| 5,683,451 A | 11/1997 | Lenker et al. | |
| 5,697,948 A | 12/1997 | Marin et al. | |
| 5,702,418 A | 12/1997 | Ravenscroft | |
| 5,709,701 A | 1/1998 | Parodi | |
| 5,722,669 A | 3/1998 | Shimizu et al. | |
| 5,723,003 A | 3/1998 | Winston et al. | |
| 5,735,869 A | 4/1998 | Fernandez-Aceytuno | |
| 5,749,848 A | 5/1998 | Jang et al. | |
| 5,749,921 A | 5/1998 | Lenker et al. | |
| 5,755,772 A | 5/1998 | Evans et al. | |
| 5,755,776 A | 5/1998 | Al-Saadon | |
| 5,755,781 A | 5/1998 | Jayaraman | |
| 5,769,882 A | 6/1998 | Fogarty et al. | |
| 5,772,669 A | 6/1998 | Vrba | |
| 5,776,141 A | 7/1998 | Klein et al. | |
| 5,800,519 A * | 9/1998 | Sandock | 623/1.22 |
| 5,807,398 A | 9/1998 | Shaknovich | |
| 5,824,040 A | 10/1998 | Cox et al. | |
| 5,824,041 A | 10/1998 | Lenker et al. | |
| 5,833,694 A | 11/1998 | Poncet | |
| 5,836,964 A | 11/1998 | Richter et al. | |
| 5,843,092 A | 12/1998 | Heller et al. | |
| 5,858,556 A | 1/1999 | Eckert et al. | |
| 5,870,381 A | 2/1999 | Kawasaki et al. | |
| 5,879,370 A | 3/1999 | Fischell et al. | |
| 5,891,190 A | 4/1999 | Boneau | |
| 5,895,398 A | 4/1999 | Wensel et al. | |
| 5,902,332 A | 5/1999 | Schatz | |
| 5,919,175 A | 7/1999 | Sirhan | |
| 5,922,020 A * | 7/1999 | Klein et al. | 623/1.15 |
| 5,961,536 A | 10/1999 | Mickley et al. | |
| 5,968,069 A | 10/1999 | Dusbabek et al. | |
| 5,976,107 A | 11/1999 | Mertens et al. | |
| 5,976,155 A | 11/1999 | Foreman et al. | |
| 5,980,484 A | 11/1999 | Ressemann et al. | |
| 5,980,486 A | 11/1999 | Enger | |
| 5,980,514 A | 11/1999 | Kupiecki et al. | |
| 5,980,552 A | 11/1999 | Pinchasik et al. | |
| 5,984,957 A | 11/1999 | Laptewicz, Jr. et al. | |
| 6,007,517 A | 12/1999 | Anderson | |
| 6,022,359 A | 2/2000 | Frantzen | |
| 6,033,434 A | 3/2000 | Borghi | |
| 6,039,721 A | 3/2000 | Johnson et al. | |
| 6,042,589 A | 3/2000 | Marianne | |
| 6,056,722 A | 5/2000 | Jayaraman | |
| 6,066,155 A | 5/2000 | Amann et al. | |
| 6,068,655 A | 5/2000 | Seguin et al. | |
| 6,090,063 A * | 7/2000 | Makower et al. | 604/13 |
| 6,090,136 A | 7/2000 | McDonald et al. | |
| 6,102,942 A | 8/2000 | Ahari | |
| 6,106,530 A | 8/2000 | Harada | |
| RE36,857 E | 9/2000 | Euteneuer et al. | |
| 6,120,522 A | 9/2000 | Vrba et al. | |
| 6,123,712 A | 9/2000 | Di Caprio et al. | |
| 6,123,723 A | 9/2000 | Konya et al. | |
| 6,126,685 A | 10/2000 | Lenker et al. | |
| 6,129,756 A | 10/2000 | Kugler et al. | |
| 6,143,016 A | 11/2000 | Bleam et al. | |
| 6,165,167 A | 12/2000 | Delaloye | |
| 6,179,878 B1 | 1/2001 | Duering | |
| 6,187,034 B1 | 2/2001 | Frantzen | |
| 6,190,402 B1 | 2/2001 | Horton et al. | |
| 6,196,995 B1 | 3/2001 | Fagan | |
| 6,200,337 B1 | 3/2001 | Moriuchi et al. | |
| 6,241,691 B1 | 6/2001 | Ferrera et al. | |
| 6,251,132 B1 | 6/2001 | Ravenscroft et al. | |
| 6,251,134 B1 | 6/2001 | Alt et al. | |
| 6,254,612 B1 | 7/2001 | Hieshima | |
| 6,254,628 B1 | 7/2001 | Wallace et al. | |
| 6,258,117 B1 | 7/2001 | Camrud et al. | |
| 6,267,783 B1 | 7/2001 | Letendre et al. | |
| 6,273,913 B1 | 8/2001 | Wright et al. | |
| 6,312,458 B1 | 11/2001 | Golds | |
| 6,315,794 B1 | 11/2001 | Richter | |
| 6,319,277 B1 | 11/2001 | Rudnick et al. | |
| 6,325,823 B1 | 12/2001 | Horzewski et al. | |
| 6,357,104 B1 | 3/2002 | Myers | |
| 6,375,676 B1 | 4/2002 | Cox | |
| 6,383,171 B1 | 5/2002 | Gifford et al. | |
| 6,419,693 B1 | 7/2002 | Fariabi | |
| 6,451,025 B1 * | 9/2002 | Jervis | 606/108 |
| 6,451,050 B1 | 9/2002 | Rudakov et al. | |
| 6,468,298 B1 | 10/2002 | Pelton | |
| 6,468,299 B2 | 10/2002 | Stack et al. | |
| 6,485,510 B1 * | 11/2002 | Camrud et al. | 623/1.16 |
| 6,488,694 B1 | 12/2002 | Lau et al. | |
| 6,511,468 B1 * | 1/2003 | Cragg et al. | 604/508 |
| 6,520,987 B1 | 2/2003 | Plante | |
| 6,527,789 B1 | 3/2003 | Lau et al. | |
| 6,527,799 B2 | 3/2003 | Shanley | |
| 6,555,157 B1 | 4/2003 | Hossainy | |
| 6,575,993 B1 | 6/2003 | Yock | |
| 6,582,394 B1 | 6/2003 | Reiss et al. | |
| 6,592,549 B2 | 7/2003 | Gerdts et al. | |
| 6,599,296 B1 | 7/2003 | Gillick et al. | |
| 6,602,282 B1 | 8/2003 | Yan | |
| 6,605,062 B1 | 8/2003 | Hurley et al. | |
| 6,645,547 B1 | 11/2003 | Shekalim et al. | |
| 6,656,212 B2 | 12/2003 | Ravenscroft et al. | |
| 6,666,883 B1 | 12/2003 | Seguin et al. | |
| 6,679,909 B2 | 1/2004 | McIntosh et al. | |
| 6,692,465 B2 | 2/2004 | Kramer | |
| 6,702,843 B1 | 3/2004 | Brown | |
| 6,712,827 B2 | 3/2004 | Ellis et al. | |
| 6,712,845 B2 | 3/2004 | Hossainy | |
| 6,723,071 B2 | 4/2004 | Gerdts et al. | |

| | | |
|---|---|---|
| 6,743,251 B1 | 6/2004 | Eder |
| 6,800,065 B2 | 10/2004 | Duane et al. |
| 6,849,084 B2 | 2/2005 | Rabkin et al. |
| 2001/0020154 A1 | 9/2001 | Bigus et al. |
| 2001/0020181 A1 | 9/2001 | Layne |
| 2001/0044595 A1 | 11/2001 | Reydel et al. |
| 2002/0037358 A1 | 3/2002 | Barry et al. |
| 2002/0138132 A1 | 9/2002 | Brown |
| 2002/0151955 A1 | 10/2002 | Tran et al. |
| 2002/0156496 A1 | 10/2002 | Chermoni |
| 2002/0188343 A1 | 12/2002 | Mathis |
| 2002/0188347 A1 | 12/2002 | Mathis |
| 2003/0045923 A1 | 3/2003 | Bashiri et al. |
| 2003/0093143 A1 | 5/2003 | Zhao et al. |
| 2003/0114919 A1 | 6/2003 | McQuiston et al. |
| 2003/0114922 A1 | 6/2003 | Iwasaka et al. |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0176909 A1 | 9/2003 | Kusleika |
| 2003/0199821 A1 | 10/2003 | Gerdts et al. |
| 2003/0225446 A1 | 12/2003 | Hartley |
| 2004/0087965 A1 | 5/2004 | Levine et al. |
| 2004/0093061 A1 | 5/2004 | Acosta et al. |
| 2004/0093067 A1 | 5/2004 | Israel |
| 2004/0098081 A1 | 5/2004 | Landreville et al. |
| 2004/0186551 A1 | 9/2004 | Kao et al. |
| 2004/0215165 A1 | 10/2004 | Coyle et al. |
| 2004/0215312 A1 | 10/2004 | Andreas |
| 2004/0249435 A1 | 12/2004 | Andreas et al. |
| 2005/0010276 A1 | 1/2005 | Acosta et al. |
| 2005/0038505 A1 | 2/2005 | Shulze et al. |
| 2005/0133164 A1 | 6/2005 | Andreas et al. |
| 2005/0149159 A1 | 7/2005 | Andreas et al. |
| 2005/0288763 A1 | 12/2005 | Andreas et al. |
| 2006/0229700 A1 | 10/2006 | Acosta et al. |
| 2006/0282147 A1 | 12/2006 | Andreas et al. |
| 2006/0282150 A1 | 12/2006 | Olson et al. |

FOREIGN PATENT DOCUMENTS

| | | |
|---|---|---|
| EP | 274129 B1 B1 | 7/1988 |
| EP | 282143 | 9/1988 |
| EP | 0 505 686 | 9/1992 |
| EP | 0 533 960 | 3/1993 |
| EP | 0 596 145 | 5/1997 |
| EP | 0 947 180 A | 10/1999 |
| EP | 947180 | 10/1999 |
| WO | WO96/33677 | 10/1996 |
| WO | WO97/46174 | 12/1997 |
| WO | WO97/48351 | 12/1997 |
| WO | WO97/48351 A1 | 12/1997 |
| WO | WO99/01087 | 1/1999 |
| WO | WO 00/15151 A1 | 3/2000 |
| WO | WO 00/32136 A1 | 6/2000 |
| WO | WO 00/41649 | 7/2000 |
| WO | WO 00/62708 | 10/2000 |
| WO | WO 00/72780 | 12/2000 |
| WO | WO 01/70297 | 9/2001 |
| WO | WO 01/91918 | 12/2001 |
| WO | WO 03/022178 A1 | 3/2003 |
| WO | WO 03/051425 | 6/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 | 6/2004 |

OTHER PUBLICATIONS

Colombo, "The Invatec Bifurcation Stent Solution" Bifurcation Stents: Novel Solutions, TCT 2003, Washington: Sep. 15-19, 2003, 24 pages total.

Lefevre et al. "Approach to Coronary Bifurcation Stenting in 2003," Euro PCR, (May 2003) 28 pages total.

"Stent". Definitionas from Dictionary.com. Unabridged (v1.01). Retrieved Sep. 22, 2006, from Dictionary.com website: <http://dictionary.reference.com/search?q=stent>.

Stimpson et al, Parallel Production of Oligonucleotide Arrays Using Membranes and Reagent Jet Printing, BioTechniques 25:886-890 (Nov. 1998).

* cited by examiner

APPARATUS AND METHODS FOR DELIVERING COILED PROSTHESES

CROSS-REFERENCES TO RELATED APPLICATIONS

The present application is a non-provisional of U.S. patent application Ser. No. 60/336,767, filed Dec. 3, 2001, the full disclosure of which is incorporated herein by reference.

BACKGROUND OF THE INVENTION

1. Field of the Invention.

The present invention relates generally to medical devices and methods. More particularly, the present invention relates to apparatus and methods for independently delivering a plurality of luminal prostheses within a body lumen, such as a blood vessel.

Coronary artery disease is the leading cause of death and morbidity in the United States and Western society. In particular, atherosclerosis in the coronary arteries can cause myocardial infarction, commonly referred to as a heart attack, which can be immediately fatal or even if survived, cause damage to the heart which can incapacitate the patient.

While coronary artery bypass surgery can be an effective treatment for stenosed arteries resulting from atherosclerosis or other causes, it is a highly invasive, costly procedure, which typically requires substantial hospital and recovery time. Percutaneous transluminal coronary angioplasty, commonly referred to as balloon angioplasty, is less invasive, less traumatic, and significantly less expensive than bypass surgery. Heretofore, however, balloon angioplasty has not been considered as effective a treatment as bypass surgery. The effectiveness of balloon angioplasty, however, has improved significantly with the introduction of stenting, which involves the placement of a scaffold structure within the artery which has been treated by balloon angioplasty. The stent inhibits abrupt reclosure of the artery and has some benefit in inhibiting subsequent restenosis resulting from hyperplasia. Recently, experimental trials have demonstrated that coating stents with anti-proliferative drugs, such as paclitaxel, can significantly reduce the occurrence of hyperplasia in angioplasty treated coronary arteries which have been stented with the coated stents.

While the combination of balloon angioplasty with drug-coated stents holds great promise, significant challenges still remain. Of particular interest to the present invention, the treatment of extended or disseminated disease within an artery remains problematic. Most stents have a fixed length, typically in the range from 10 mm to 30 mm, and the placement of multiple stents to treat disease over a longer length requires the successive use of multiple balloon stent delivery catheters. Moreover, it can be difficult to stent an angioplasty-treated region of a blood vessel with the optimum stent length.

For these reasons, it would be desirable to provide improved stents, stent delivery systems, stenting methods, and the like, for the treatment of patients having coronary artery disease, as well as other occlusive diseases of the vasculature. In particular, it would be desirable to provide stents, delivery systems, and methods for the treatment of disseminated and variable length stenotic regions within the vasculature. For example, it would be desirable to provide methods which permit a physician to optimize the length of the treated vessel which is stented according to the nature of the disease, either by adjusting the stent length in situ or by placing multiple stents of the same or different lengths over the treatment region. At least some of these objectives will be met by the inventions described hereinafter.

2. Description of the Background Art.

U.S. Pat. No. 6,190,402B1, describes a self-forming vascular implant. U.S. Pat. No. 6,258,117, describes a multiple section stent structure; and U.S. Pat. No. 5,895,398, describes a clot retrieval device having a deployable helical clot snare.

BRIEF SUMMARY OF THE INVENTION

The present invention provides for improved methods, apparatus, and systems for delivering prostheses to body lumens, particularly stents and grafts to blood vessels in the arterial and venous vasculature. The prostheses comprise scaffold structures formed from linearized elements, typically metal wires having a round diameter, but also including ribbons, multifilar cables, braided structures, composite structures, wires having non-circular cross-sections, and the like. By "linearized element," it is meant that the structural component will be capable of assuming a linearized configuration while the scaffold is being delivered. Most simply, the linearized element will have a non-linear configuration when unconstrained and will assume the linearized configuration when subjected to radial or axial constraint. In such instances, the linearized element will be formed so that it has a "memory" of the non-linear configuration but can be linearized by applying compressive or axial stress. In the exemplary embodiment, the linearized element has a helical memory. When constrained within the lumen of a delivery device, the linearized element assumes a generally straight configuration. When advanced outwardly from the constrained lumen, however, the linearized element returns to its helical configuration. A number of metals will have efficient elasticity to be able to shift between the linearized and non-linear configurations. Some of the metals include spring stainless steels, such as MP35N, Elgiloy, as well as super-elastic alloys, such as nickel-titanium alloys, e.g. Nitinol™ alloy.

While the presently preferred linearized element will be formed from an elastic metal, one skilled in the art will appreciate that a variety of other metal and non-metal materials could be used to form such elements. For example, the elements could be formed from malleable metals, such as malleable stainless steel alloys, where the linearized element is then deformed into the non-linear configuration as it is advanced from the delivery device, e.g., by passing the linearized element over a shaping mandrel in the delivery device. Alternatively, the linearized element could be formed from a heat memory alloy, where the element is heated in situ after deployment in order to effect the change in shape from linear to non-linear. In addition, resilient and malleable polymeric and other non-metal materials might find use. These technologies, as well as others, for changing the shape of metal and non-metal structures within body lumens, are well described in the technical and medical literature.

The linearized elements of the present invention will be capable of assuming a variety of non-linear configurations. While helical non-linear configurations are presently preferred, it will be appreciated that serpentine, zigzag and other irregular configurations would also be suitable for at least some of the intended purposes of the present invention. Moreover, while it will generally be preferred to form the linearized elements from wire, most usually wire having a circular cross-section, it will also be possible to form the linearized elements from ribbons, flat sheets of material, and other conventional techniques. For example, serpentine or zigzag non-linearized elements could be formed from flat sheets of appropriate metal, e.g. by laser cutting, chemical etching, or the like. For example, a flat sheet could be configured to assume a desired tubular geometry.

Methods according to the present invention for delivering prostheses to a body lumen comprise introducing a delivery device to an interior of the body lumen, typically the lumen of a blood vessel, where the device carries the linearized element, as discussed above. The element is deployed by advancing the element relative to the delivery device within the interior of the body lumen so that the element assumes its non-linear configuration across the surface region of the interior as the element is advanced. The element is then released from the delivery device after it has assumed its non-linear configuration. Release may be effected by selectively severing the element after a desired length of the element has been reached. Alternatively, the delivery device may carry a plurality of linearized elements, each having a desired length so that each individual element is released after its entire length has been advanced from the delivery device.

Advancing the linearized element relative to the delivery device may comprise drawing the delivery device proximally relative to the body lumen while pushing the linearized element from the delivery device, typically using an internal pusher element. In such instances, the pusher rod will usually be held in a generally stationary relationship to the body lumen, while the delivery device is retracted proximally relative to both the body lumen and the pusher rod. In this way, the linearized element will deploy within the body lumen, while assuming its nonlinear configuration, with little or no relative movement relative to the luminal wall. This is desirable since any movement of the linearized element against the luminal wall may cause injury, particularly in arteries and other blood vessels.

In order to even further reduce movement of the deploying linearized element against the vessel wall, and thus reducing the risk of trauma to the vessel wall, it will often be desirable to control the deployment to offset the foreshortening of the linearized element as it is deployed. It will be appreciated that when a linearized element assumes a non-linear configuration, such as a helical configuration, the absolute length of the element will shorten. In the case of helical elements, the shortening will be quite significant, typically from 80 percent to 99 percent, depending on the pitch of the helix which is released. In order to minimize motion of the element against the vessel wall as it is deployed, it is therefore desirable to move the delivery device approximately at a rate substantially equal to the axial progress of the deployed helix within the body lumen (which will be much less than the absolute length of the linearized element which is being expelled). Thus, the pusher rod will be moving in a distal direction which is more rapid than the proximal withdrawal of the delivery device. Moreover, it will be further desirable to rotate the delivery device so that the deploying "helical" element is not caused to rotate within the vessel. Thus, three separate parameters of the deployment will need to be controlled to minimize the relative motion of the helical element against the blood vessel wall. First, the delivery device will be withdrawn proximally at a rate equal to the axial rate of deployment of the helix within the blood vessel. Second, the pusher rod will be distally advanced at a rate equal to the linear deployment rate of the helix within the deployment device. Finally, rotation of the delivery device will be controlled to counteract any tendency of the delivery device to rotate the helix as it is being deployed. All three of these deployment parameters may be manually controlled by the physician by observing the deployment under fluoroscopic imaging. Alternatively, programmable systems may be provided to automatically deploy and control the element deployment.

In a specific aspect of the method of the present invention, the pitch of the helical element may be controlled by adjusting the rate of drawing the delivery device proximally and/or advancing the linearized element from the delivery device. While the helical configuration of the linearized device will usually have a preferred or natural pitch, the actual pitch within the blood vessel or the body lumen may be controlled to a certain degree by adjusting its rate of advancement and the withdrawal rate of the delivery device to adjust the pitch. Usually, the delivery device will be rotated in order to further control the release geometry of the linearized element.

In other specific aspects of the method of the present invention, the prostheses are selectively deployed to traverse desired lengths of the vasculature or other body lumen. The covered length can be controlled in either or both of two ways. First, when the delivery device has the ability to sever the linearized element, the treating physician can control the length of prostheses by simply starting at a first target location, deploying the prostheses as described above (optionally with control of pitch in a helical prostheses), and severing the prostheses from the delivery device when a desired end location has been reached.

Additionally, the length of the vessel to be treated may be controlled by delivering multiple helical or other prostheses at selected and distributed portions of the luminal wall. Again, the treating physician will choose a beginning point within the body lumen and then deliver a prostheses over a selected length of the body lumen from that point. One, two, three, four or more additional segments of the prostheses may then be deployed.

Thus, the methods and apparatus of the present invention can be used to treat both short and long diseased segments within the vasculature and other body lumens. Usually, the treated regions will have a length of at least 10 mm and may have a length up to 60 mm and in some instances 100 mm or longer. Typically, when using only a single deployed prostheses, the treated lengths will be from 10 mm to 50 mm, usually from 10 mm to 30 mm. When using multiple prostheses, the lengths may be much greater, typically from 20 mm to 100 mm, more often from 20 mm to 60 mm.

As a further option, the linearized elements of the present invention may be coated, loaded, or otherwise coupled to or with an active substance intended to enhance the selected therapy. Linearized elements intended for treating blood vessels and other body lumens may be coated with substances intended to inhibit cellular proliferation, inflammation, or other conditions. Exemplary active substances include anti-neoplastic drugs such as paclitaxel, methotrexate, and batimastal; antibiotics such as doxycycline, tetracycline, rapamycin, and actinomycin; immunosuppressants such as dexamethosone, methyl prednisolone, nitric oxide sources such as nitroprussides; estrogen; estradiols; and the like.

The present invention further comprises catheters and other apparatus for delivering helical prostheses. The catheters comprise a catheter body having a proximal end, a distal end, and at least one lumen through at least a portion thereof. A linearized element is disposed in the lumen, and the mechanism for advancing and releasing at least one length of the linearized element from the lumen is provided. As described above, the linearized elements will assume a non-linear configuration when advanced and released from the catheter body. Usually, the advancing and releasing mechanism will comprise a severing mechanism to selectively cut the linearized element after a desired length has been released. Alternatively, the catheter may carry a plurality of linearized elements which are divided or cut into discrete lengths prior to deployment. Thus, the discrete lengths may be released after they are fully advanced from the lumen of the catheter body. In the latter case, the catheter body may carry from two to twenty discrete elements, typically from three to ten discrete elements.

DETAILED DESCRIPTION OF THE INVENTION

Figure 1:
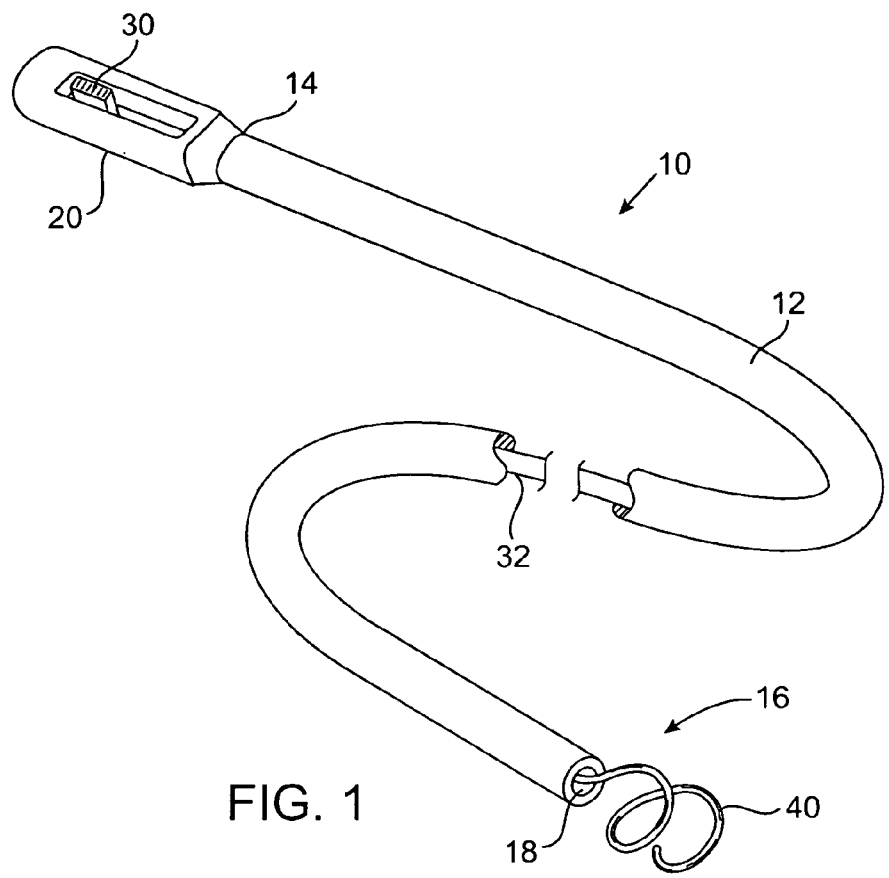
FIG. 1 is a perspective view of a catheter capable of delivering helical elements constructed in accordance with the principles of the present invention.

Referring to FIG. 1, a delivery device comprising a catheter 10 includes a catheter body 12 having a proximal end 14 and a distal end 16. The catheter will include at least one lumen 18 (FIG. 2) extending over at least a portion thereof, and will further include a proximal hub 20 attached to the proximal end 14. Hub 14 will include a mechanism for advancing a linearized element 26 from the lumen 18, such as a thumb slide 30. In the exemplary embodiment, the thumb slide will be attached to a push rod 32 which extends through the lumen 18 and engages the linearized element(s) 40 to be advanced from the catheter. As shown in FIG. 1, the linearized element 40 assumes a helical non-linear configuration as it is advanced from the lumen 18 of the catheter body 12.

Figure 2:
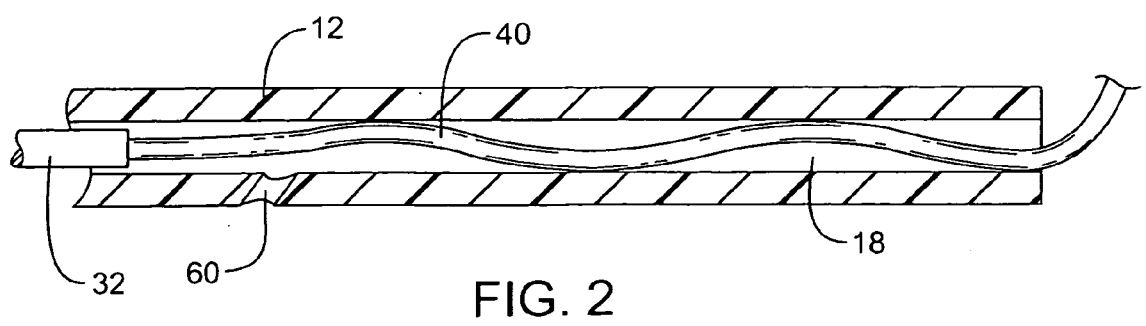
FIG. 2 is a detailed view of the distal end of the catheter of FIG. 1, shown in section.
Figure 1A:
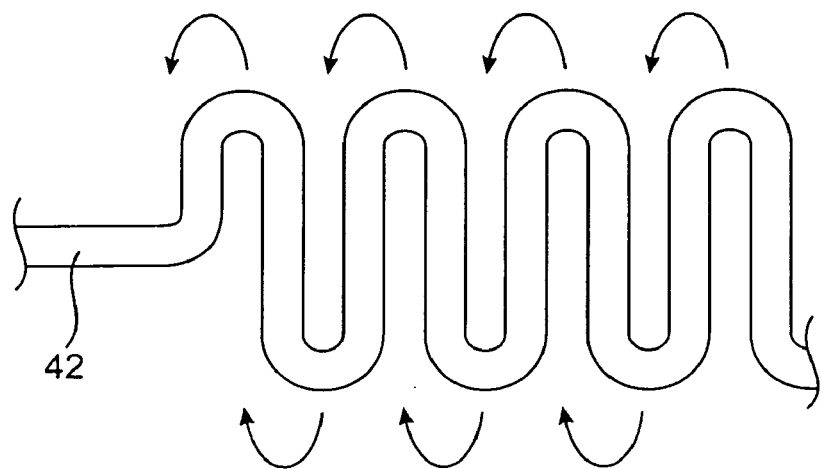
FIGS. 1A and 1B illustrate alternatively non-linearized element geometries according to the present invention.
Figure 1B:
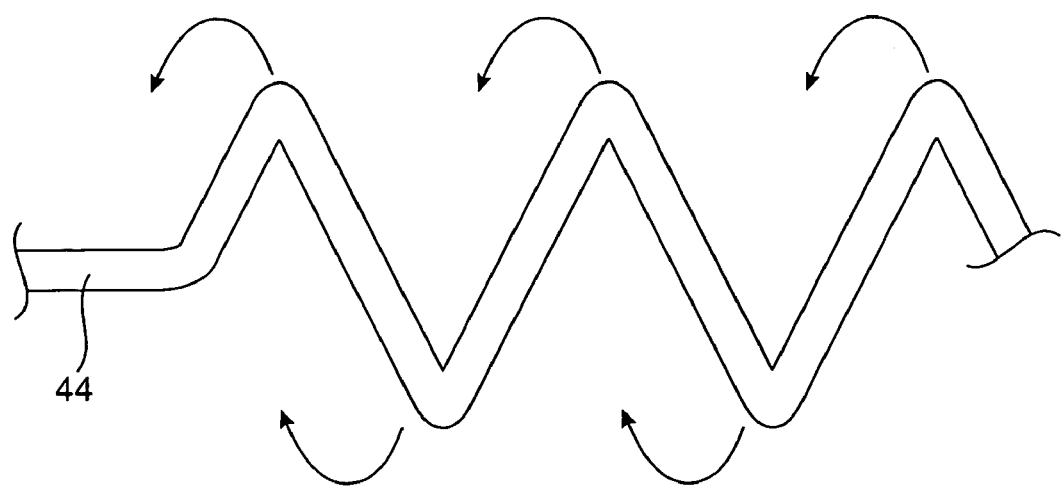

Referring now to FIG. 1A, an alternative linearized element 42 is illustrated which will assume a serpentine non-linear configuration when advanced from the catheter or other delivery device. FIG. 1A shows the serpentine structure in its flattened or "rolled-out" configuration. It will be appreciated that the scaffold provided by the serpentine structure will be rolled into a generally tubular configuration, as indicated by the arrows in FIG. 1A. When linearized, the element 42 will still assume a generally straight configuration, as shown in FIG. 2. A second alternative non-linear geometry comprises the zigzag pattern shown in FIG. 1B. Again, FIG. 1B illustrates this pattern in its flattened or rolled-out configuration. The actual device would be rolled as indicated by the arrows into a generally tubular configuration to serve as a scaffold structure in the present invention.

As illustrated in FIG. 2, a single linearized element 40 is pushed by the pusher rod 32 to assume its helical or rather non-linear configuration when fully released from the catheter body 12. Since the linearized element 40 and the pusher rod 42 are not connected, there is no need to provide a severing or other release mechanism in the embodiment of FIG. 2.

Figure 3:
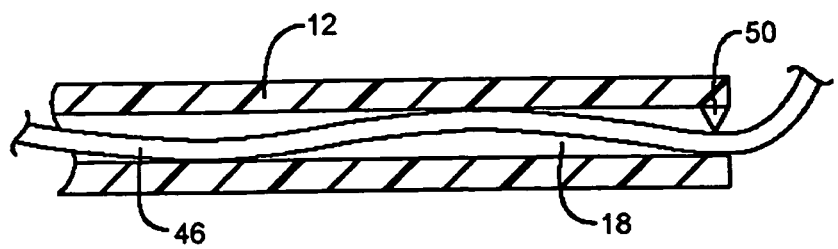
FIG. 3 is an alternative view of the distal end of the catheter of FIG. 1, shown in section.

FIG. 3, in contrast, shows a linearized element 46 having an indeterminate length. That is, the linearized element 46 will be sufficiently long so that it may be divided into two, three, four, or an even larger number of discrete non-linearized elements upon release from the catheter body 12. In order to effect such release, a severing device 50, such as an actuable blade, electrochemical, or other severing mechanism, is provided at the distal end of the delivery device. In this way, once a non-linear structure having a sufficient length has been delivered, the transition point between the linearized element and the non-linearized element will be severed using the device 50. Additional non-linear scaffold devices may then be delivered using the same catheter over regions spaced apart within the vasculature or other body lumens.

Figure 4:
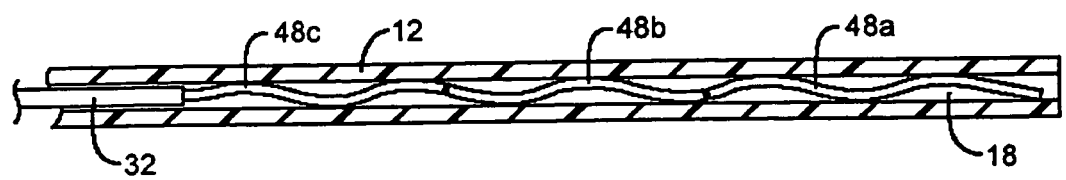
FIG. 4 is a second alternative view of the distal end of the catheter of FIG. 1, shown in section.

Referring now to FIG. 4, a third alternative advancement and release mechanism is illustrated. The embodiment of FIG. 4 is similar to that of FIG. 2, except that a plurality of discrete linearized elements 48a, 48b, and 48c, are carried within lumen 18 and advanced using pusher rod 32. It will be appreciated that since these linearized elements 48a-48c are separate, and unconnected, they may be released sequentially by advancing the pusher rod (and optionally retracting and/or rotating the catheter body 12) to deliver each non-linearized element. There is no need to provide for a severing mechanism as with the embodiment of FIG. 3. While three discrete linearized elements 48a-48c are illustrated, it will be appreciated that anywhere from two to 10 linearized elements, or more, could be accommodated using the approach of FIG. 4.

Figure 5E:
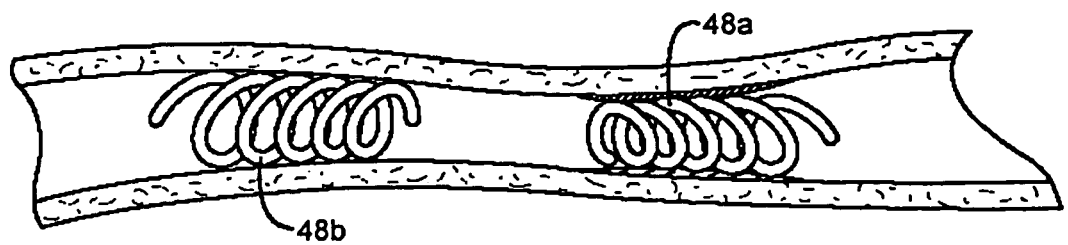
FIGS. 5A-5E illustrate use of the catheter of FIG. 1 for delivering multiple, helical prostheses at distributed points in the blood vessel.
Figure 5A:
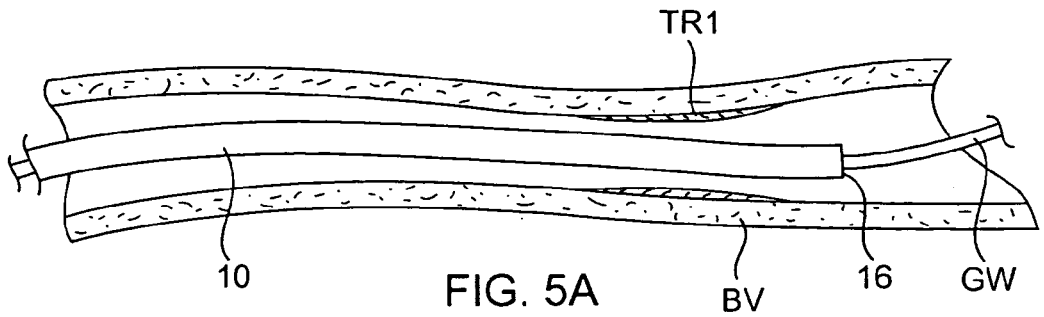
Figure 5B:
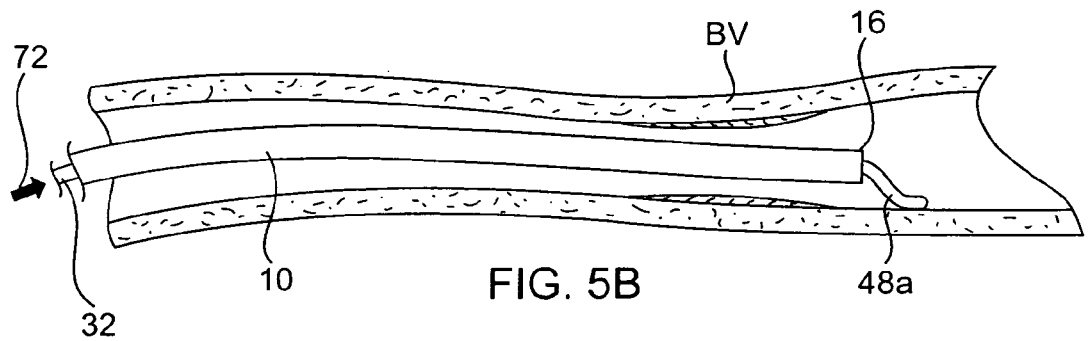
Figure 5C:
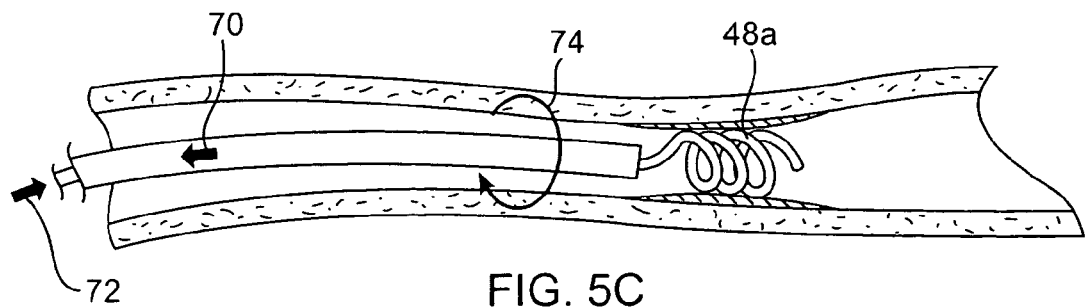

Referring now to FIGS. 5A-5C, use of the delivery catheter 10 of FIG. 3 or FIG. 4 will be illustrated. Catheter 10 is initially delivered so that its distal end 16 lies past a first target region TR1, as shown in FIG. 5A. The catheter 10 may be introduced over a guide wire GW. The catheter may be an over-the-wire design. In some instances, however, it will be preferable to provide a rapid exchange design having a side guide wire port 60 spaced a short distance from its distal end, as shown in FIG. 2. In this way, the catheter may be introduced by withdrawing the pusher rod 32 and linearized element proximally so that they lie behind the side guide wire 60. The catheter may then be introduced over the conventional guide wire GW without the need to completely remove and/or exchange the pusher rod and linearized element assembly with the guide wire. Of course, for catheters having larger diameters, it would be possible to provide a separate guide wire lumen extending the entire length of the catheter for an over-the-wire introduction.

Once the catheter 10 is in place, the pusher rod 32 will be advanced so that the first non-linearized element 48 is advanced from the distal end 16, as illustrated in FIG. 5B. The pusher rod is pushed in the direction of the arrow and a leading end of the element 48c engages the luminal wall of the blood vessel BV.

After the element 48c engages the luminal wall, it is desirable to begin retracting the catheter body in the direction of arrow 70 while advancing the pusher rod 32 in the direction of arrow 72 while preferably rotating the catheter body to counteract the relative rotation of the element 48c. The catheter body is thus rotated in the direction of arrow 74. By appropriately controlling each of these three motions, the coil will deploy helically with minimal motion relative to the luminal wall.

Figure 5D:
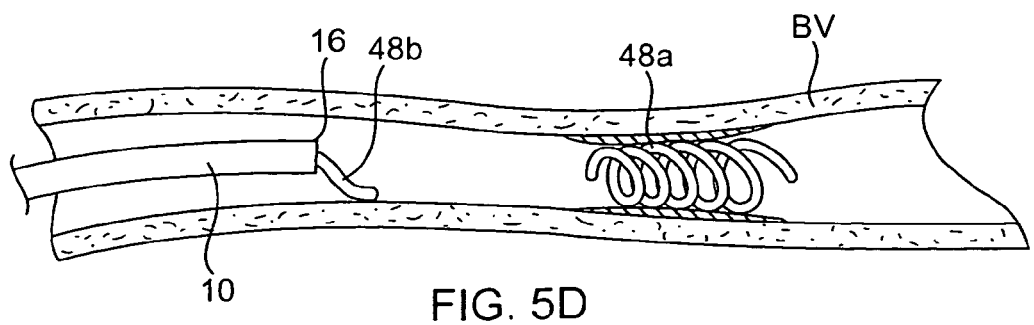

The first prostheses 48a will be completely delivered when it is advanced fully from the distal end 16 of catheter 10, as illustrated in FIG. 5D. The catheter 10 may continue to be withdrawn through the vasculature or other body lumen until a second region is reached where it is desired to deliver the second element 48b. The steps of delivering the second linearized element 48b from the catheter are analogous to those described in FIGS. 5A-5C for the first element 48a. A complete deployment of the first linearized element 48a into its helical configuration and the second linearized element 48b into its helical configuration are illustrated in FIG. 5E.

It will be appreciated that the lengths, pitches, adjacent spacings, and the like, of the helical and other elements deployed according to the methods of the present invention can be controlled at the discretion of the treating physician. Thus, the methods and apparatus of the present invention provide useful flexibility for the treating physician to treat extended and disseminated disease in the vasculature and other body lumens.

Although the foregoing invention has been described in some detail by way of illustration and example, for purposes of clarity of understanding, it will be obvious that certain changes and modifications may be practiced within the scope of the appended claims.

What is claimed is:

1. A method for delivering a prosthesis to a stenotic region of a blood vessel, said method comprising:
    introducing a delivery device to an interior of the blood vessel, wherein said device carries a plurality of discrete helical element, each of the plurality of discrete helical elements having a predetermined length and being separable from the remainder of helical elements;
    advancing a first number of the discrete helical elements relative to the delivery device within the interior of the blood vessel, wherein advancing comprises drawing and rotating the delivery device relative to the body lumen while pushing the first number of discrete helical elements from the delivery device and wherein the first number of the discrete helical elements assume a helical configuration which traverses a surface region of the interior of the blood vessel as the first number is advanced;
    viewing the length of the first number relative to the length of the stenotic region;
    selecting a first number of a discrete helical elements so that the combined length of the first number of discrete helical elements with a separate element coupled to the catheter matches the length of the stenotic region of the blood vessel, the first number being operator selectable between 1 and at least 2;
    separating the first number of discrete helical elements from a second number of discrete helical elements;
    releasing the first number of the one or more discrete helical elements in the non-linear configuration from the delivery device into the stenotic region of the blood vessel, wherein upon release the first number forms and remains a generally tubular scaffold to inhibit closure of the stenotic region without substantially inhibiting blood flow through the blood vessel; and
    maintaining the second number of the discrete helical elements in the delivery device after the first number is released;
    wherein the first number of discrete helical elements assumes a helical configuration and the delivery device is rotated as the first number of discrete helical elements are pushed.

2. A method for delivering a prosthesis to a stenotic region of a blood vessel, the method comprising:
    introducing an elongate catheter shaft having a proximal end, a distal end and a lumen therebetween into the blood vessel, the shaft carrying a self-expandable prosthetic element disposed in the lumen in a linearized configuration while constrained in the lumen and adapted to radially expand into a helical configuration upon deployment, and wherein the prosthetic element is separable into a first prosthesis having a first length and second prostheses having a second length prior to release from the catheter shaft;
    advancing the first length of the prosthetic element from the lumen while the second length is retained in the lumen in the linearized configuration; and
    separating the first prosthesis from the second prosthesis with a separating element coupled to the catheter shaft such that the first prosthesis resiliently expands to the helical configuration outside the lumen while the second prosthesis is retained in the catheter shaft in the linearized configuration, the helical configuration being generally tubular with an open longitudinal passage therein adapted to provide a scaffold to inhibit closure of the blood vessel without substantially inhibiting blood flow through the longitudinal passage, wherein the first prosthesis continuously engages a wall of the blood vessel along substantially all of the first length.

3. A method according to claim 2, wherein separating comprises severing the first prosthesis from the second prosthesis after the first prosthesis has traversed the stenotic region.

4. A method according to claim 2, further comprising viewing the first prosthesis relative to the length of the stenotic region.

5. A method according to claim 2, wherein advancing comprises drawing the catheter shaft relative to the blood vessel and pushing the first prosthesis from the lumen as the catheter shaft is drawn.

6. A method according to claim 5, wherein the rate of drawing the catheter shaft is varied relative to the rate of pushing the first prosthesis from the catheter shaft catheter in order to control the pattern in which the first prosthesis is laid on the stenotic region.

7. A method according to claim 5, wherein the rate of drawing the delivery catheter is varied relative to the rate of pushing the first prosthesis from the delivery catheter in order to control the pitch of the first prosthesis.

8. A method according to claim 5, further comprising rotating the catheter shaft as the first prosthesis is pushed.

9. A method according to claim 2, wherein the prosthetic element is at least partially malleable and wherein advancing comprises deforming the first prosthesis into the helical configuration as the first prosthesis is advanced.

10. A method according to 2, wherein the prosthetic element is pre-shaped with a spring memory and wherein advancing comprising releasing the first prosthesis from a linearized constraint.

11. A method according to claim 10, wherein the constraint is the lumen and wherein advancing comprises pushing the first prosthesis from the lumen as the catheter shaft is drawn relative to the body lumen.

12. A method according to claim 11, wherein the rate of drawing the catheter shaft is varied relative to the rate of pushing the first prosthesis in order to control the pattern in which the first prosthesis is laid on the stenotic region.

13. A method according to claim 12, wherein the first prosthesis is advanced so that it traverses the stenotic region with diffuse disease over a length of at least 10 mm.

14. A method according to claim 12, wherein the element is coated or loaded with an active substance which inhibits hyperplasia after the first prosthesis has been placed in the blood vessel.

15. A method according to claim 2, wherein the prosthetic element is composed at least partly of a bioabsorbable material.

16. A method according to claim 15, Wherein the prosthetic element comprises a metal scaffold covered with a polymeric layer.

17. A method according to claim 2, wherein the first length is different than the second length.

* * * * *